United States Patent
Blanco et al.

(10) Patent No.: US 11,058,504 B2
(45) Date of Patent: Jul. 13, 2021

(54) CONTROL ARM ASSEMBLIES FOR ROBOTIC SURGICAL SYSTEMS

(71) Applicant: Covidien LP, Mansfield, MA (US)

(72) Inventors: Matthew Blanco, Boston, MA (US); Andres Chamorro, Ashland, MA (US); Peter Vokrot, Malden, MA (US); Robert Pierce, Franklin, MA (US); William Peine, Ashland, MA (US)

(73) Assignee: COVIDIEN LP, Mansfield, MA (US)

( * ) Notice: Subject to any disclaimer, the term of this patent is extended or adjusted under 35 U.S.C. 154(b) by 245 days.

(21) Appl. No.: 16/306,420

(22) PCT Filed: Jun. 2, 2017

(86) PCT No.: PCT/US2017/035583
§ 371 (c)(1),
(2) Date: Nov. 30, 2018

(87) PCT Pub. No.: WO2017/210501
PCT Pub. Date: Dec. 7, 2017

(65) Prior Publication Data
US 2020/0315729 A1  Oct. 8, 2020

Related U.S. Application Data

(60) Provisional application No. 62/345,505, filed on Jun. 3, 2016.

(51) Int. Cl.
*G05G 9/047* (2006.01)
*A61B 34/00* (2016.01)
(Continued)

(52) U.S. Cl.
CPC ............. *A61B 34/74* (2016.02); *A61B 34/25* (2016.02); *A61B 34/37* (2016.02); *B25J 9/0087* (2013.01);
(Continued)

(58) Field of Classification Search
CPC ........ A61B 34/74; A61B 34/25; B25J 9/1689; B25J 13/02; B25J 3/00
See application file for complete search history.

(56) References Cited

U.S. PATENT DOCUMENTS 5,137,198 A * 8/1992 Nobis .................. A61B 17/072
227/175.3
7,391,177 B2 6/2008 Kishi et al.
(Continued)

FOREIGN PATENT DOCUMENTS

WO 2012127404 A2 9/2012
WO 2013018934 A1 2/2013
(Continued)

OTHER PUBLICATIONS

Chinese First Office Action dated Nov. 28, 2019 corresponding to counterpart Patent Application CN 201780002018.7.
(Continued)

*Primary Examiner* — Jake Cook

(57) ABSTRACT

A control arm assembly for controlling a robot system includes a gimbal that is moveable and rotatable about three axes, and a handle assembly coupled to the gimbal. The handle assembly includes a body portion having a controller disposed therein and a first actuator disposed thereon. The first actuator is mechanically coupled to the controller via a four-bar linkage such that actuation of the first actuator causes mechanical movement of a component of the controller which is converted by the controller into an electrical signal.

16 Claims, 7 Drawing Sheets

(51) Int. Cl.
*A61B 34/37* (2016.01)
*B25J 9/00* (2006.01)
*B25J 9/10* (2006.01)
*B25J 9/16* (2006.01)
*B25J 13/06* (2006.01)
*F16H 21/54* (2006.01)

(52) U.S. Cl.
CPC ............. *B25J 9/106* (2013.01); *B25J 9/1664* (2013.01); *B25J 13/06* (2013.01); *F16H 21/54* (2013.01)

(56) References Cited

U.S. PATENT DOCUMENTS

| | | |
|---|---|---|
| 8,828,023 B2 | 9/2014 | Neff et al. |
| 2004/0186345 A1 | 9/2004 | Yang et al. |
| 2008/0068372 A1 | 3/2008 | Krah |
| 2009/0245600 A1 | 10/2009 | Hoffman et al. |
| 2010/0321482 A1 | 12/2010 | Cleveland |
| 2012/0150349 A1 | 6/2012 | Rust et al. |
| 2013/0006268 A1 | 1/2013 | Swarup et al. |
| 2014/0007732 A1 | 1/2014 | Ogawa |
| 2014/0160015 A1 | 6/2014 | Ogawa et al. |
| 2017/0172675 A1 | 6/2017 | Jarc et al. |
| 2019/0223968 A1 | 7/2019 | Jarc et al. |

FOREIGN PATENT DOCUMENTS

| | | |
|---|---|---|
| WO | 2013018984 A2 | 2/2013 |
| WO | 2017075121 A1 | 5/2017 |
| WO | 2017100434 A1 | 6/2017 |

OTHER PUBLICATIONS

Chinese Second Office Action dated Sep. 1, 2020 corresponding to counterpart Patent Application CN 201780002018.7.
Partial European Search Report dated Jan. 15, 2020 corresponding to counterpart Patent Application EP 17807282.3.
Extended European Search Report dated Jan. 20, 2020 corresponding to counterpart Patent Application EP 17807531.3.
International Search Report and Written Opinion of corresponding counterpart Int'l Appln. No. PCT/US17/035583 dated Sep. 12, 2017.
Extended European Search Report dated Apr. 22, 2020 corresponding to counterpart Patent Application EP 17807282.3.

* cited by examiner

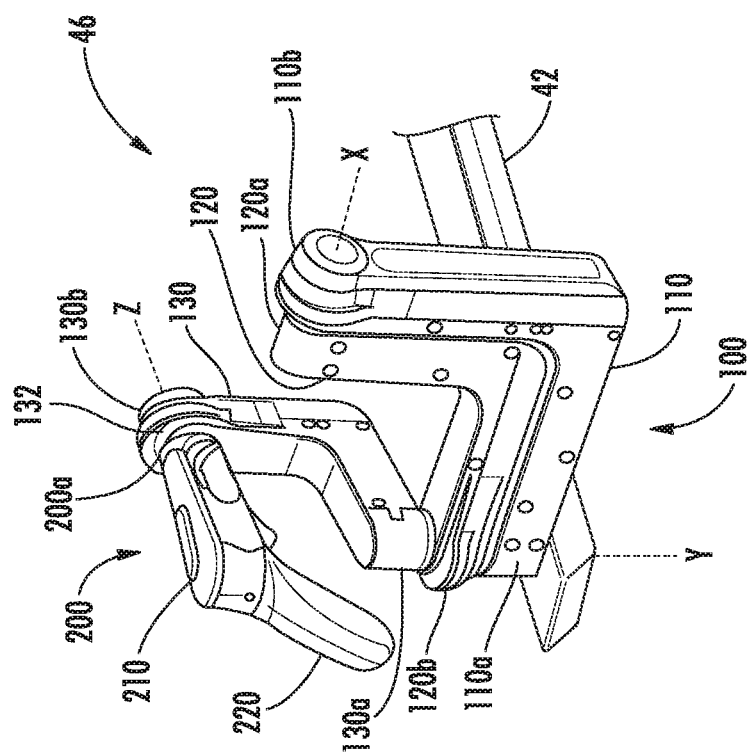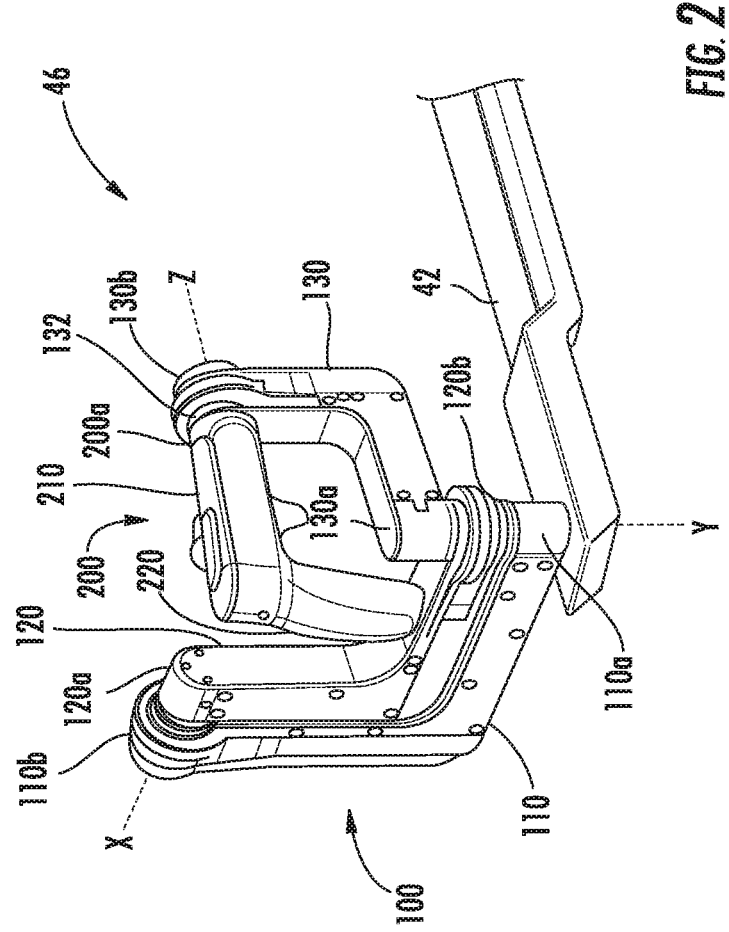
FIG. 2

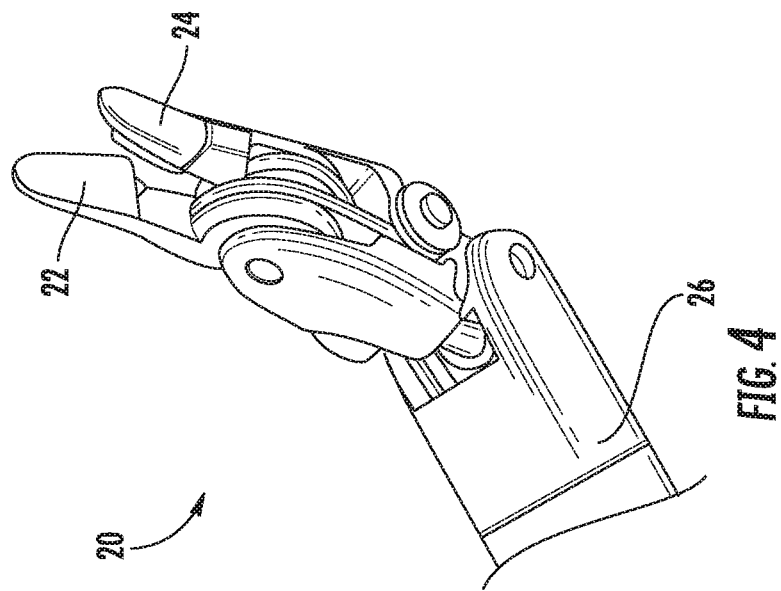
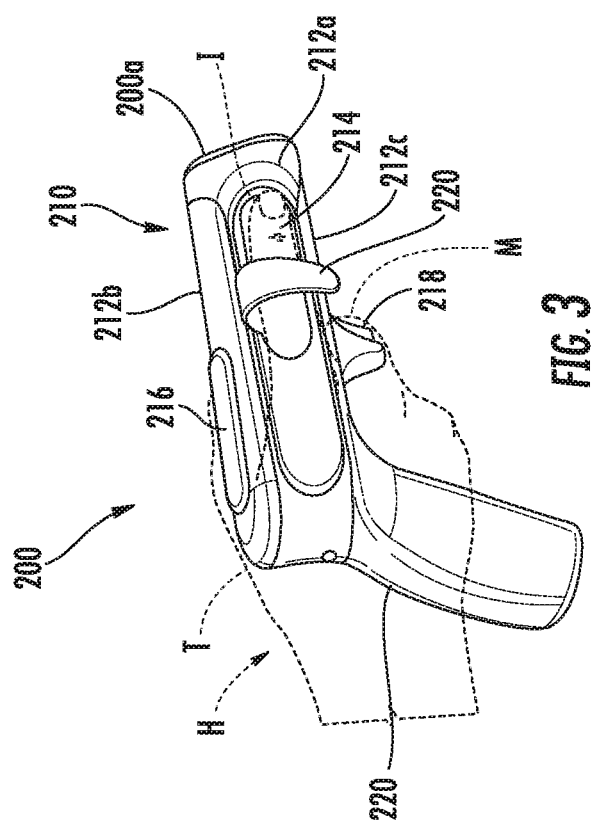

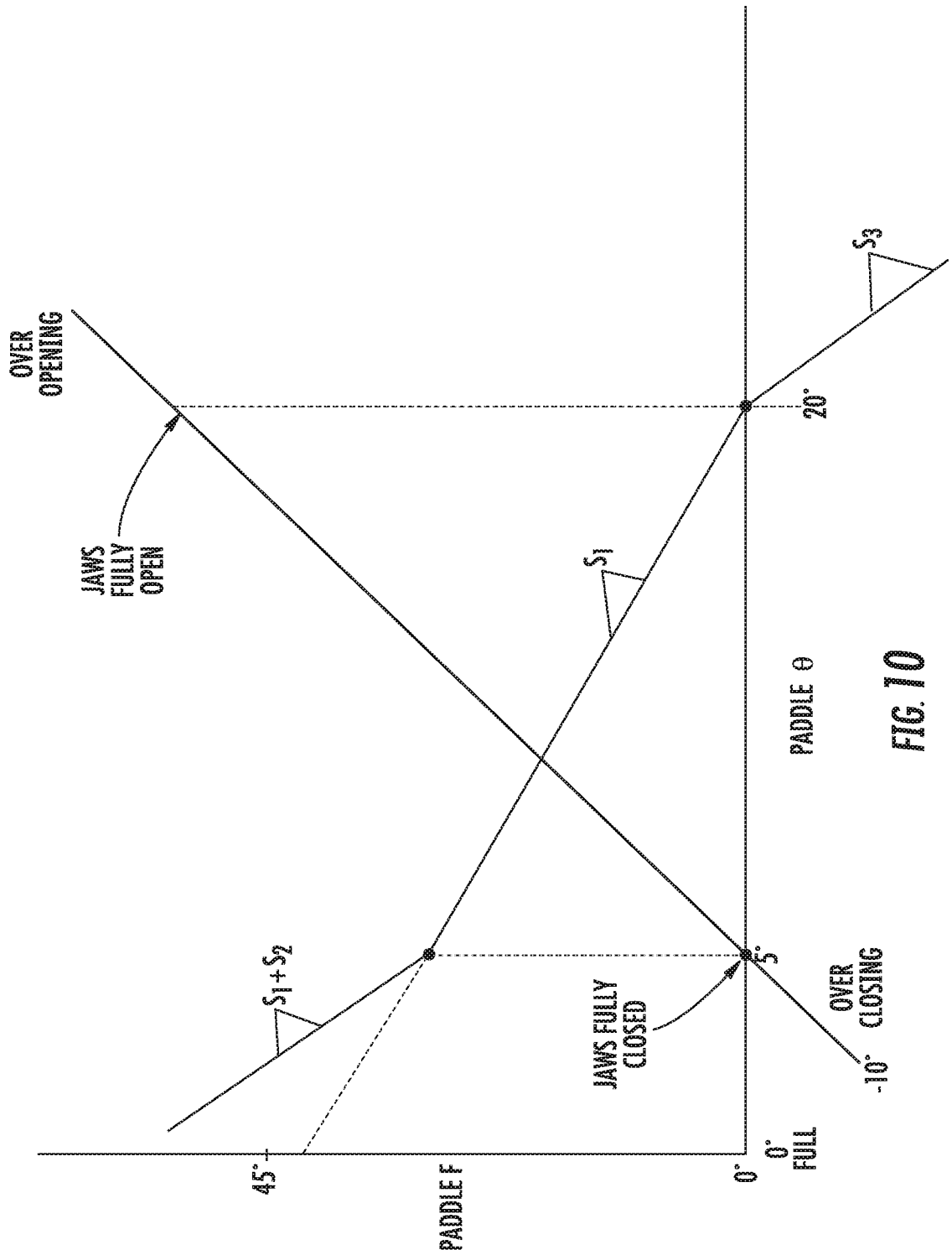

CONTROL ARM ASSEMBLIES FOR ROBOTIC SURGICAL SYSTEMS

CROSS-REFERENCE TO RELATED APPLICATIONS

This application is a U.S. National Stage Application filed under 35 U.S.C. § 371(a) of International Patent Application Serial No. PCT/US2017/035583, filed Jun. 2, 2017, which claims the benefit of and priority to U.S. Provisional Patent Application Ser. No. 62/345,505, filed Jun. 3, 2016, the entire disclosure of which is incorporated by reference herein.

BACKGROUND

Robotic surgical systems have been used in minimally invasive medical procedures. During such medical procedures, a robotic surgical system is controlled by a surgeon interfacing with a user interface. The user interface allows the surgeon to manipulate an end effector of a robot system that acts on a patient. The user interface includes a control arm assembly that is moveable by the surgeon to control the robotic surgical system.

There is a need for improved control arm assemblies for moving and operating the end effector of the robotic surgical system.

SUMMARY

The present disclosure relates generally to control arm assemblies of a user interface of a robotic surgical system that allows a clinician to control a robot system of the robotic surgical system during a surgical procedure. Handle assemblies of the control arm assemblies include finger-controlled actuators configured to allow a clinician to comfortably interface with the control arm assemblies for controlling an arm and/or a tool of the robot system, and gimbals of the control arm assemblies include connectors configured to allow a clinician to easily connect/disconnect the handle assemblies to/from the control arm assemblies.

In one aspect of the present disclosure, a control arm assembly for controlling a robot system includes a gimbal moveable and rotatable about three axes, and a handle assembly coupled to the gimbal. The handle assembly includes a body portion having a controller disposed therein and a first actuator disposed thereon. The first actuator is mechanically coupled to the controller via a four-bar linkage such that actuation of the first actuator causes mechanical movement of a component of the controller which is converted by the controller into an electrical signal.

In aspects, the first actuator includes a proximal portion and a distal portion. The first actuator can have a biased position in which the distal portion extends laterally away from the body portion. Application of a force on the distal portion in a direction towards the body portion may move the first actuator to an actuated position in which the proximal portion is moved laterally away from the body portion.

In some aspects, a first link of the four-bar linkage is secured to the proximal portion of the first actuator. In certain aspects, the four-bar linkage includes a second link fixedly disposed within the body portion of the handle assembly and operably connected to the controller, and third and fourth links pivotably coupled to the first and second links. In particular aspects, the component of the controller is a first gear, and the second link of the four-bar linkage includes a second gear attached to a shaft rotatably disposed within the second link. The second gear of the second link may be meshingly engaged with the first gear of the controller. Movement of the fourth link may cause rotational movement of the second gear of the second link which may cause rotational movement of the first gear of the controller. An end of the fourth link may be non-rotatably coupled to the second gear of the second link.

The first actuator may be disposed on an outer surface of the body portion of the handle assembly, and/or the handle assembly may include a strap extending over the distal portion of the first actuator.

In some aspects, the gimbal includes a connector releasably coupled to a distal end of the handle assembly. In certain aspects, the connector includes a flanged outer edge and opposed detents defined at terminal ends of the flanged outer edge for releasable engagement with the distal end of the handle assembly.

In another aspect of the present disclosure, a handle assembly for controlling a robot system includes a body portion, a controller disposed within the body portion, a first actuator disposed on the body portion, and a four-bar linkage mechanically coupling the controller and the first actuator such that actuation of the first actuator causes mechanical movement of a component of the controller which is converted by the controller into an electrical signal.

In aspects, the first actuator includes a proximal portion and a distal portion. The first actuator can have a biased position in which the distal portion extends laterally away from the body portion. Application of a force on the distal portion in a direction towards the body portion may move the first actuator to an actuated position in which the proximal portion is moved laterally away from the body portion.

In some aspects, a first link of the four-bar linkage is secured to the proximal portion of the first actuator. In certain aspects, the four-bar linkage further includes a second link fixedly disposed within the body portion and operably connected to the controller, and third and fourth links pivotably coupled to the first and second links. In particular aspects, the component of the controller is a first gear, and the second link of the four-bar linkage includes a second gear attached to a shaft rotatably disposed within the second link. The second gear of the second link may be meshingly engaged with the first gear of the controller. Movement of the fourth link may cause rotational movement of the second gear of the second link which may cause rotational movement of the first gear of the controller. An end of the fourth link may be non-rotatably coupled to the second gear of the second link.

The first actuator may be disposed on an outer surface of the body portion, and/or the handle assembly may include a strap extending over the distal portion of the first actuator.

Other aspects, features, and advantages will be apparent from the description, drawings, and the claims.

BRIEF DESCRIPTION OF THE DRAWINGS

Various aspects of the present disclosure are described herein below with reference to the drawings, which are incorporated in and constitute a part of this specification, wherein:

FIG. 2 is an enlarged perspective view of the two control arm assemblies of the user interface of FIG. 1;

FIG. 3 is a perspective view of a handle assembly of one of the control arm assemblies of FIG. 2, with a hand of a clinician shown in phantom;

FIG. 4 is a perspective view of a tool of the robot system of FIG. 1 in accordance with an embodiment of the present disclosure;

FIG. 10 is a graph showing jaw angle and paddle force vs paddle angle in accordance with an embodiment of the present disclosure;

DETAILED DESCRIPTION

Figure 1:
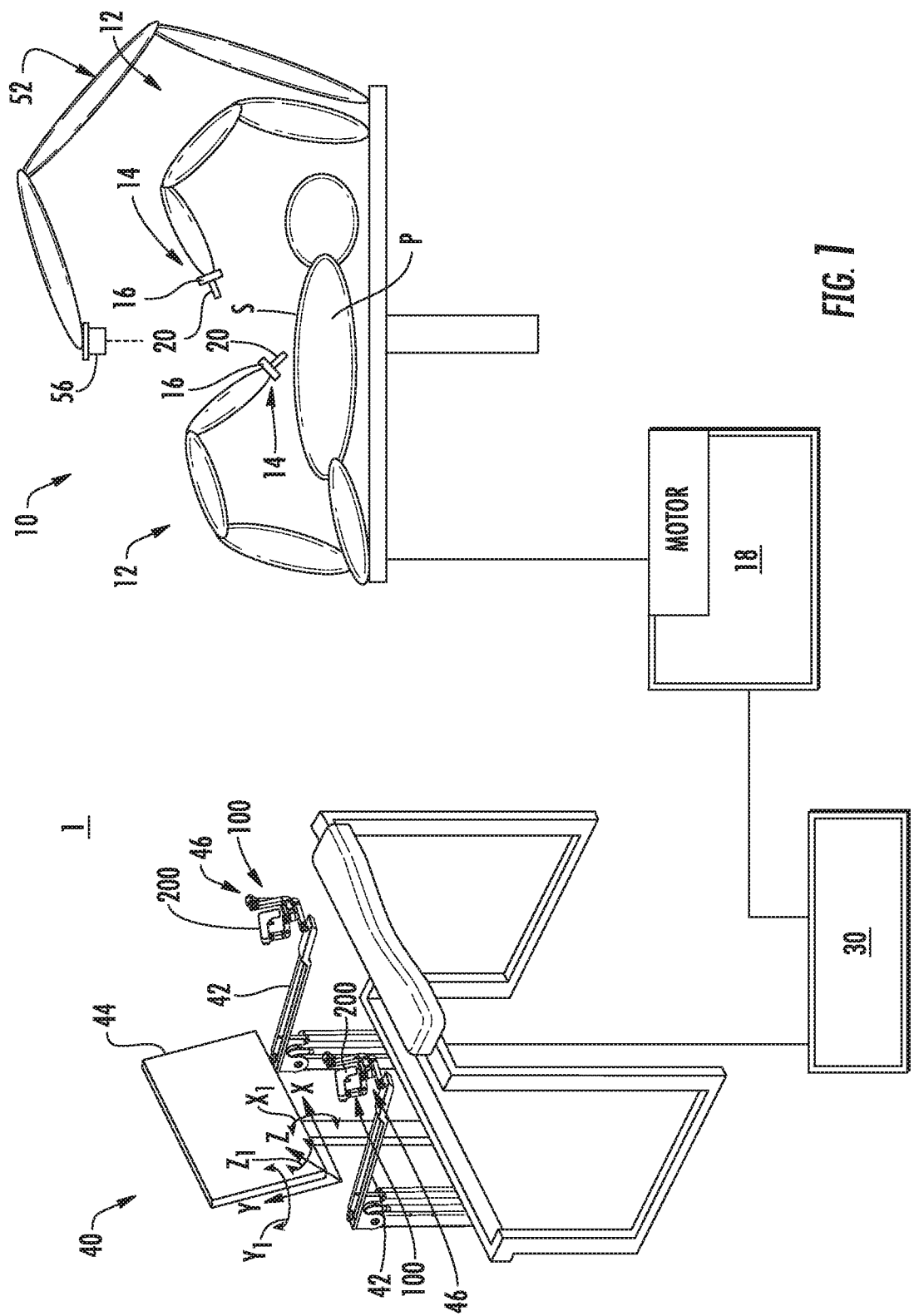
FIG. 1 is a schematic illustration of a robotic surgical system including a robot system and a user interface having two control arm assemblies in accordance with an embodiment of the present disclosure.

Embodiments of the present disclosure are now described in detail with reference to the drawings in which like reference numerals designate identical or corresponding elements in each of the several views. As used herein, the term "clinician" refers to a doctor, nurse, or any other care provider and may include support personnel. Throughout this description, the term "proximal" refers to a portion of a system, device, or component thereof that is closer to a hand of a clinician, and the term "distal" refers to a portion of the system, device, or component thereof that is farther from the hand of the clinician.

Turning now to FIG. 1, a robotic surgical system 1 in accordance with the present disclosure is shown. The robotic surgical system 1 includes a robot system 10, a processing unit 30, and an operating console or user interface 40. The robot system 10 generally includes linkages 12 and a robot base 18. The linkages 12 moveably support an end effector or tool 20 which is configured to act on tissue of a patient "P" at a surgical site "S." The linkages 12 may form arms, each arm 12 having an end 14 that supports the tool 20. In addition, the ends 14 of each of the arms 12 may include an imaging device 16 for imaging the surgical site "S," and/or a tool detection system (not shown) that identifies the tool 20 (e.g., a type of surgical instrument) supported or attached to the end 14 of the arm 12.

The processing unit 30 electrically interconnects the robot system 10 and the user interface 40 to process and/or send signals transmitted and/or received between the user interface 40 and the robot system 10, as described in further detail below.

The user interface 40 includes a display device 44 which is configured to display three-dimensional images. The display device 44 displays three-dimensional images of the surgical site "S" which may include data captured by imaging devices 16 positioned on the ends 14 of the arms 12 and/or include data captured by imaging devices that are positioned about the surgical theater (e.g., an imaging device positioned within the surgical site "S," an imaging device positioned adjacent the patient "P", an imaging device 56 positioned at a distal end of an imaging arm 52). The imaging devices (e.g., imaging devices 16, 56) may capture visual images, infra-red images, ultrasound images, X-ray images, thermal images, and/or any other known real-time images of the surgical site "S." The imaging devices 16, 56 transmit captured imaging data to the processing unit 30 which creates three-dimensional images of the surgical site "S" in real-time from the imaging data and transmits the three-dimensional images to the display device 44 for display.

The user interface 40 includes control arms 42 which support control arm assemblies 46 to allow a clinician to manipulate the robot system 10 (e.g., move the arms 12, the ends 14 of the arms 12, and/or the tools 20). The control arm assemblies 46 are in communication with the processing unit 30 to transmit control signals thereto and to receive feedback signals therefrom which, in turn, transmit control signals to, and receive feedback signals from, the robot system 10 to execute a desired movement of robot system 10.

Each control arm assembly 46 includes a gimbal 100 operably coupled to the control arm 42 and an input device or handle assembly 200 operably coupled to the gimbal 100. Each of the handle assemblies 200 is moveable through a predefined workspace within a coordinate system having "X," "Y," and "Z" axes to move the ends 14 of the arms 12 within a surgical site "S." The three-dimensional images on the display device 44 are orientated such that the movement of the gimbals 100, as a result of the movement of the handle assemblies 200, moves the ends 14 of the arms 12 as viewed on the display device 44. It will be appreciated that the orientation of the three-dimensional images on the display device 44 may be mirrored or rotated relative to a view from above the patient "P." In addition, it will be appreciated that the size of the three-dimensional images on the display device 44 may be scaled to be larger or smaller than the actual structures of the surgical site "S" to permit a clinician to have a better view of structures within the surgical site "S." For a detailed discussion of scaling of handle assembly movement, reference may be made to commonly owned U.S. Provisional Patent Application Ser. No. 62/265,457, filed Dec. 10, 2015, now International Patent Application Serial No. PCT/US16/65588, filed Dec. 8, 2016, the entire content of each of which is incorporated herein by reference. As the handle assemblies 200 are moved, the tools 20 are moved within the surgical site "S." It should be understood that movement of the tools 20 may also include movement of the arms 12 and/or the ends 14 of the arms 12 which support the tools 20.

For a detailed discussion of the construction and operation of a robotic surgical system 1, reference may be made to U.S. Pat. No. 8,828,023, the entire contents of which are incorporated herein by reference.

Referring now to FIG. 2, each gimbal 100 of the control arm assemblies 46 includes an outer link 110, an intermediate link 120, and an inner link 130. The outer link 110 includes a first end 110a pivotably connected to the control arm 42 and a second end 110b pivotably connected to a first end 120a of the intermediate link 120 such that the intermediate link 120 is rotatable, as indicated by arrow "$X_1$" (FIG. 1), about the "X" axis. The intermediate link 120 includes a second end 120b pivotably connected to a first end 130a of the inner link 130 such that the inner link 130 is rotatable, as indicated by arrow "$Y_1$" (FIG. 1), about the "Y" axis. The inner link 130 includes a second end 130b having a connector 132 configured to releasably engage a distal end 200a of the handle assembly 200 such that the handle assembly 200 is rotatable, as indicated by arrow "$Z_1$" (FIG. 1), about the "Z" axis. In embodiments, the outer, intermediate, and inner links 110, 120, 130 are each substantially L-shaped frames that are configured to nest within each other. However, it should be understood that the outer, intermediate, and inner links 110, 120, 130 may be any shape so long as the "X," "Y," and "Z" axes are orthogonal to each other in the zero or home position (see e.g., FIG. 2).

As shown in FIGS. 2 and 3, the handle assembly 200 of each of the control arm assemblies 46 includes a body portion 210 and a grip portion 220. The body portion 210 includes a housing 212 supporting a plurality of actuators 214, 216, 218 for controlling various functions of the tool 20 (FIG. 4) of the robot system 10 (FIG. 1). As illustrated and oriented in FIG. 3, the first actuator 214 is disposed on an outer side surface 212a of the housing 212, the second actuator 216 is disposed on a top surface 212b of the housing 212, and the third actuator 218 extends from a bottom surface 212c of the housing 212 to form a trigger. It should be understood that the actuators 214, 216, 218 can have any suitable configuration (e.g., buttons, knobs, toggles, slides, rockers, etc.), and placement of the actuators 214, 216, 218 about the handle assembly 200 may vary. The first actuator 214 includes a finger rest 222 and a strap 224 extending over the finger rest 222 to secure a finger (e.g., the index finger) of the clinician's hand to the first actuator 214 so that the handle assembly 200 does not slide relative to the finger.

Each handle assembly 200 allows a clinician to manipulate (e.g., clamp, grasp, fire, open, close, rotate, thrust, slice, etc.) the respective tool 20 supported at the end 14 of the arm 12 (FIG. 1). As shown, for example, in FIG. 4, the tool 20 may be a jaw assembly including opposed jaw members 22, 24 extending from a tool shaft 26. The first actuator 214 may be configured to actuate the jaw members 22, 24 of the tool 20 between open and closed configurations, as described in further detail below. The second and third actuators 216, 218 effect other functions of the tool 20, such as fixing the configuration of the jaw members 22, 24 relative to one another, rotating the jaw members 22, 24 relative to the tool shaft 26, firing a fastener (not shown) from one of the jaw members 22, 24, actuating a knife (not shown) disposed within one of the jaw members 22, 24, activating a source of electrosurgical energy such that electrosurgical energy is delivered to tissue via the jaw members 22, 24, among other functions within the purview of those skilled in the art.

Figure 5:
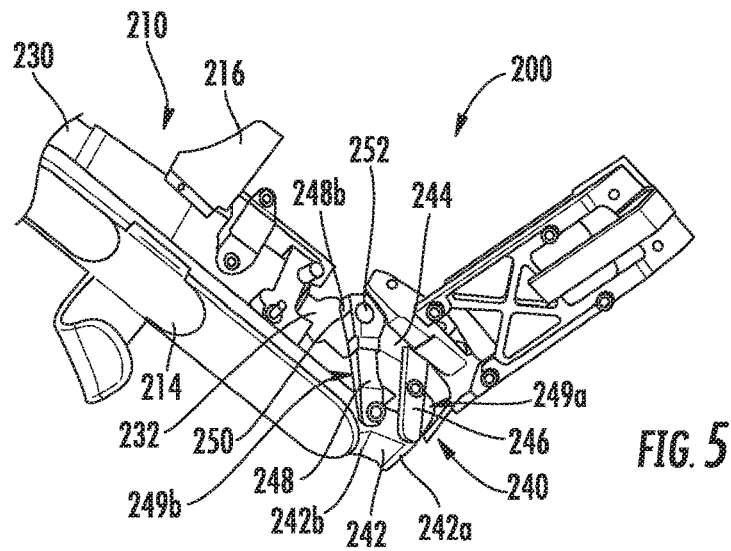
FIGS. 5 and 6 are perspective views, with parts removed, of the handle assembly of FIG. 3.
Figure 6:
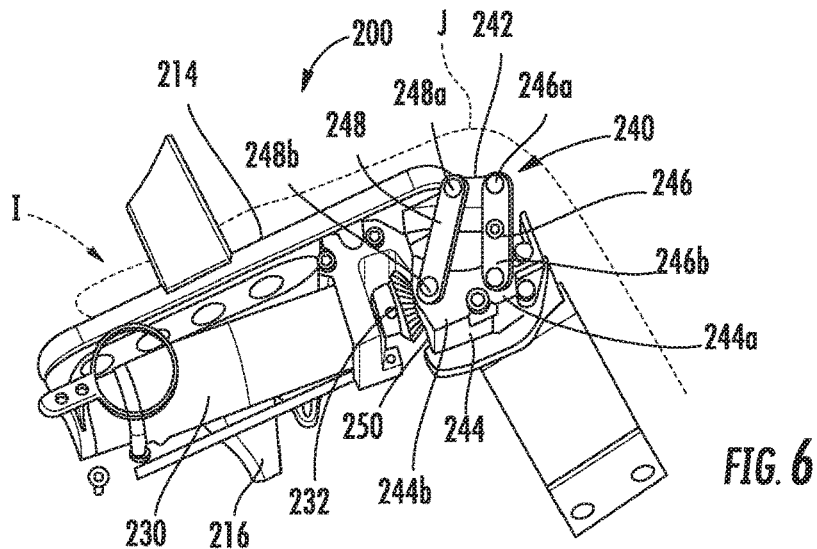
Figure 7:
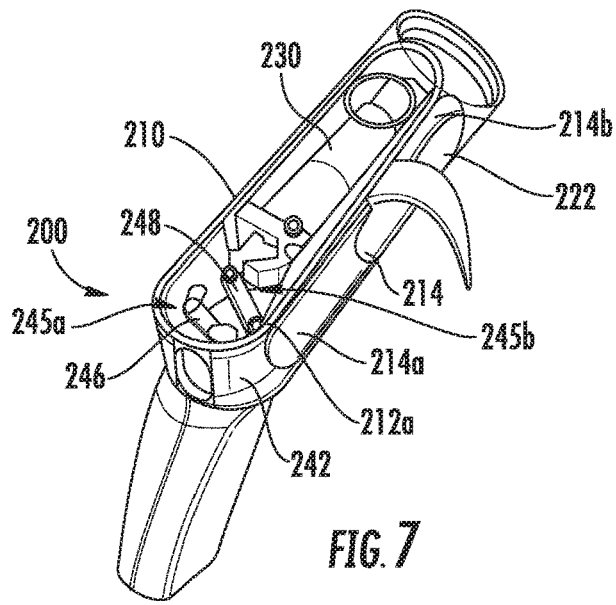
FIG. 7 is a top perspective view, with parts removed, of the handle assembly of FIGS. 3, 5, and 6, with an index finger of a hand of a clinician shown in phantom.

As shown in FIG. 5-7, a controller 230 is disposed within the body portion 210 of the handle assembly 200 such that actuation of the first, second, and/or third actuator 214, 216, 218 (FIG. 3) actuates the controller 230 which converts mechanical movement of the first, second, and/or third actuators 214, 216, 218 into electrical signals for processing by the processing unit 30 (FIG. 1) which, in turn, sends electrical signals to the robot system 10 (FIG. 1) to actuate a function of the tool 20 (FIG. 1). It should be understood that the robot system 10 may send signals to the processing unit 30 and thus, to the controller 230 to provide feedback to a clinician operating the handle assembly 200.

The first actuator 214 is mechanically coupled to the controller 230 by a four-bar linkage 240. The four-bar linkage 240 includes a first link 242, a second link 244, a third link 246, and a fourth link 248. The third and fourth links 246, 248 are each pivotably coupled to the first and second links 242, 244. Each of the third and fourth links 246, 248 includes an upper link portion 245a, 249a and a lower link portion 245b, 249b, respectively.

The first link 242 extends proximally from the first actuator 214. A first end 246a of the third link 246 is pivotally connected to a proximal portion 242a of the first link 242 and a second end 246b of the third link 246 is pivotally connected to a proximal portion 244a of the second link 244. The second link 244 includes a gear 250 at a distal portion 244b thereof that may be keyed to a shaft 252 such that the gear 250 rotates with the shaft 252. A first end 248a of the fourth link 248 is pivotally connected to a distal portion 242b of the first link 242 and a second end 248b of the fourth link 248 is non-rotatably secured to the gear 250 and/or shaft 252 such that movement of the fourth link 248 results in rotation of the gear 250.

The first actuator 214 includes a proximal portion 214a and a distal portion 214b including the finger rest 222. In embodiments, one or more sensors 223 are embedded within the first actuator 214 such that the first actuator 214 can detect the presence or movement of a finger about the finger rest 222. Suitable sensors include, for example, touch sensors, capacitive sensors, optical sensors, and the like. The first actuator 214 has a biased position, when no force is applied to the first actuator 214, where the distal portion 214b extends laterally from the outer side surface 212a of the housing 212 of the handle assembly 200 and the proximal portion 214a is flush with, or is disposed within, the outer side surface 212a, as shown in FIG. 7.

In use, when a clinician presses on and applies force to the finger rest 222, the first actuator 214 is moved to an actuated position where the distal portion 214b of the first actuator 214 moves towards the body portion 210 of the handle assembly 200 causing the proximal portion 214a of the first actuator 214 to move laterally away from the body portion 210, resulting in a corresponding movement of the first link 242 of the four-bar linkage 240. As first link 242 is moved laterally away from the body portion 210 of the handle assembly 200, the third and fourth links 246, 248 move with respect to the second link 244 such that the fourth link 248 acts as a crank for rotating the gear 250 of the second link 244. The gear 250 of the second link 244 is meshingly engaged with a gear 232 of the controller 230 such that rotation of the gear 250 of the second link 244 causes a corresponding rotation of the gear 232 of the controller 230. The controller 230 then converts mechanical movement of the gear 232 into electronic signals including digital position and motion information, as discussed above.

The amount of force applied to the first actuator 214 by a clinician moves the first actuator 214 from the biased position to an actuated position to affect the position of the jaw members 22, 24 (FIG. 4) with respect to each other. In embodiments, the first actuator 214 is configured such that in the biased position, the jaw members 22, 24 are in a fully open position and the angular position of the first actuator 214, as measured by the controller 230, is about 20°. As a force is applied to the first actuator 214, the first actuator 214 rotates the gear 250 of the second link 244 of the four-bar linkage 240 to move the jaw members 22, 24 towards each other until they reach a fully closed position. In the fully closed position, the angular position of the first actuator 214 is less than about 5°. The four-bar linkage 240 allows a clinician to apply less force to the first actuator 214 to fully close the jaw members 22, 24 and/or maintain the jaw members 22, 24 in the fully closed position over conventional handles that require a clinician to hold the first actuator 214 at 0°. Such a configuration may, for example, minimize finger fatigue of a clinician during a surgical procedure and/or prevent over closing and over opening of the jaw members. Additionally, the first actuator 214 does not tend to slide along the finger as the first actuator 214 is actuated.

Figure 8A:
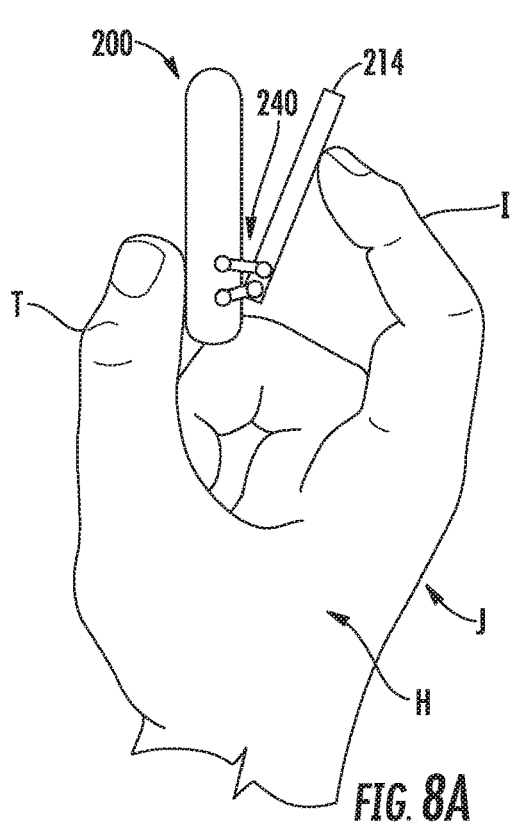
FIGS. 8A and 8B are schematic illustrations of the handle assembly of FIGS. 3 and 5-7 in a biased position and an actuated position, respectively, positioned within a hand of a clinician.
Figure 8B:
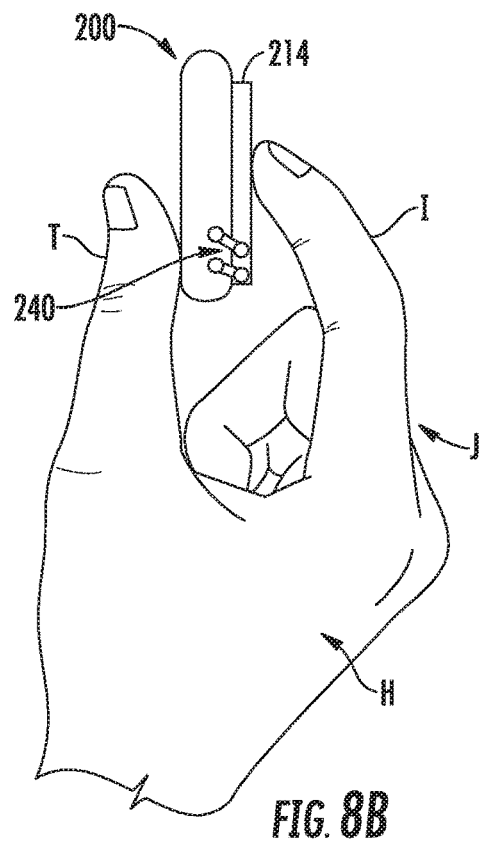
Figure 9A:
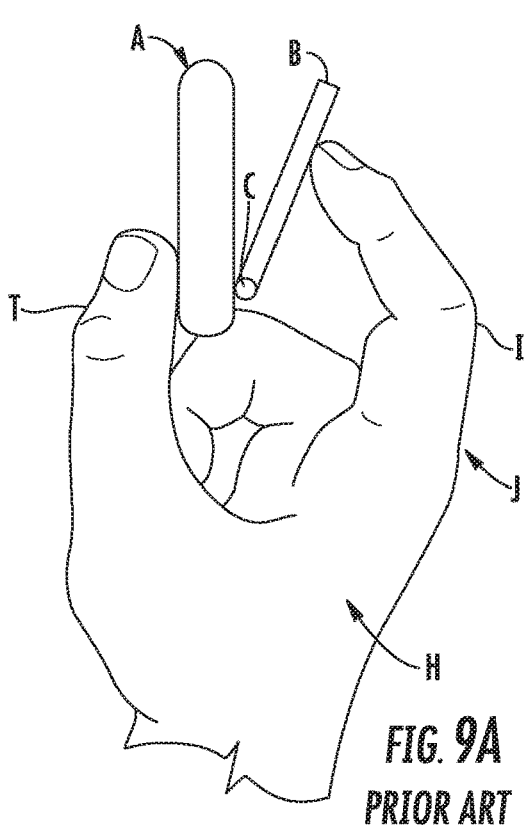
FIGS. 9A and 9B are schematic illustrations of a prior art handle assembly including an actuator having a single pivot point in a biased position and an actuated position, respectively, positioned within a hand of a clinician.
Figure 9B:
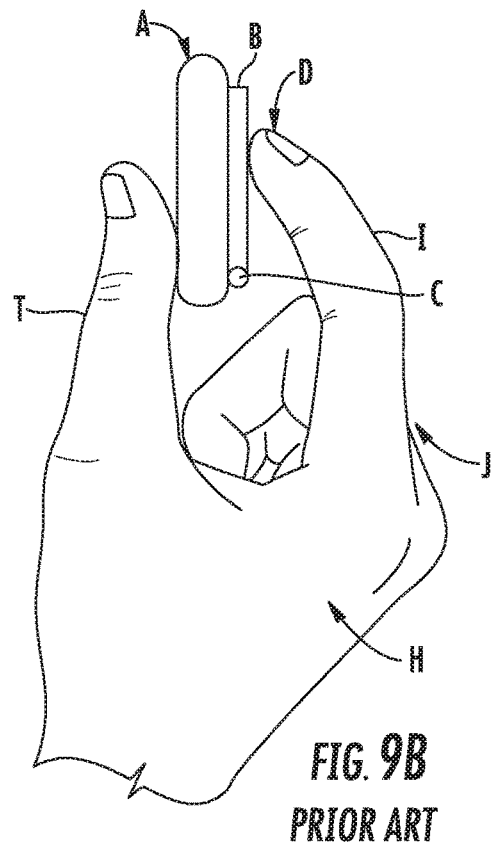

As shown in FIGS. 3 and 6, in conjunction with FIGS. 8A and 8B, a clinician grips the handle assembly 200 such that the index finger "I" (shown in phantom) of the clinician's hand "H" rests upon the first actuator 214, the palm (not shown) of the clinician's hand "H" rests on the grip portion 220 of the handle assembly 200, and the thumb "T" and the middle finger "M" of the clinician's hand "H" are free to actuate the second and third actuators 216, 218, respectively. The metacarpophalangeal joint "J" of the index finger "I" is aligned with the effective pivot point of the four-bar linkage 240 of the first actuator 214 such that the motion of the first actuator 214 moves with the index finger "I" through the range of motion between the biased position (see e.g., FIG. 8A) and the actuated position (see e.g., FIG. 8B). This alignment, as well as the pistol grip style of the handle assembly 200, allows for stable control of the handle assembly 200 and prevents sliding of the index finger "I" relative to the first actuator 214, thereby providing a more controlled feel to the handle assembly as compared to, for example as shown in FIGS. 9A and 9B, a handle assembly "A" including a first actuator "B" connected by a single pivot point "C." The pivot point "C" of the first actuator "B" is not aligned with the metacarpophalangeal joint "J" of the index finger "I" and causes longitudinal sliding, as indicated by arrow "D" in FIG. 9B, of the index finger "I" relative to the first actuator "B" during movement between the biased position (FIG. 9A) and the actuated position (FIG. 9B).

With reference to FIG. 10, a graph of the jaw angle of the tool 20 (FIG. 4) as a function of the paddle angle of the first actuator 214 (FIG. 3) is shown. The jaw members 22, 24 of the tool 20 are fully open (e.g., disposed at a predetermined jaw angle greater than 0° with respect to each other) when the first actuator 214 has a paddle angle, θ, of about 20°, and the jaw members 22, 24 are fully closed (e.g., disposed at about a 0° angle with respect to each other) when the first actuator 214 has a paddle angle, θ, of about 5°. The jaw angle curve is linear such that changes in the paddle angle, θ, of the first actuator 214 (e.g., due to movement of the first actuator 214 by a clinician) produces a corresponding and directly proportional change in the jaw angle of the tool 20.

The jaw angle curve, however, does not cross the horizontal axis at the origin. Rather, the jaw angle curve crosses the horizontal axis when the paddle angle, θ, of the first actuator 214 is about 5° and the jaw members 22, 24 are disposed in the fully closed position. Such a configuration allows the jaw members 22, 24 to be fully closed before the first actuator 214 is fully pressed which may, for example, result in less finger fatigue of a clinician during use, and also allow the jaw members 22, 24 to over-close as the paddle angle, θ, approaches 0° (e.g., the first actuator 214 is fully pressed). Over-closing the jaw members 22, 24 increases the grasping force of the tool 20 which is desired for performing surgical tasks requiring a tight hold such as, for example, retraction of stiff tissues or needle driving. Similarly, the jaw members 22, 24 may over-open as the paddle angle, θ, is brought above 20°. Over-opening the jaw members 22, 24 increases the opening force of the tool 20 which is desired for performing surgical tasks requiring additional torque to open the jaw members 22, 24 such as, for example, tissue dissection.

With continued reference to FIG. 10, paddle force as a function of the paddle angle, θ, of the first actuator 214 (FIG. 3) is also shown. Torque produced by a motor of the handle assembly 200 generates a force against which the first actuator 214 is pressed by a clinician to effect a change in the paddle angle, θ, of the first actuator 214 and thus, the jaw angle between the jaw members 22, 24. The force curve includes three linear regions having different slopes "S1", "S1+S2", and "S3". One of the regions is defined in a portion of the force curve in which the jaw members 22, 24 are disposed between the fully open and fully closed positions. The slope "S1" of this region is negative which causes the force required to close the first actuator 214 to increase as the paddle angle, θ, decreases. The force curve crosses the horizontal axis when the paddle angle, θ, of the first actuator 214 is about 20° and the jaw members 22, 24 are disposed in the fully open position. Such a configuration allows the jaw members 22, 24 to open to the fully open position, corresponding to the biased position of the first actuator 214 detailed above, but not to over-open, when a clinician's finger is removed from the first actuator 214.

Another region is defined in a portion of the force curve in which the jaw members 22, 24 are over-closed and includes the slope "S1+S2", and another region is defined in a portion of the force curve in which the jaw members 22, 24 are over-opened and includes the slope "S3". Slope "S1+S2" is steeper or greater than slope "S3". Accordingly, as a clinician presses the first actuator 214 to close the jaw members 22, 24, the force required to close the first actuator 214 increases as the first actuator 214 approaches the over-close region which, in turn, increases the stiffness in the first actuator 214 and provides a tactile indication to the clinician that the jaw members 22, 24 are entering or have entered the over-close region. Similarly, slope "S3" is steeper than slope "S1" to provide an indication to the clinician that the jaw members 22, 24 are entering or have entered the over-open region. All the values of the force are negative in each of the regions so that if the clinician's finger moves off of the first actuator 214, the jaw members 22, 24 move to the fully open position.

It should be understood that the jaw angle curve and/or the force curve may be modified to achieve different behaviors of the jaw members 22, 24 and/or the first actuator 214 in response to changes in the paddle angle of the first actuator 214 and/or to implement different desired features of the jaw members 22, 24 and/or first actuator 214. Accordingly, it is contemplated that the shape of the jaw angle curve and/or the force curve may be different for different tool types or control modes utilized with the robotic surgical system 1.

Figure 11:
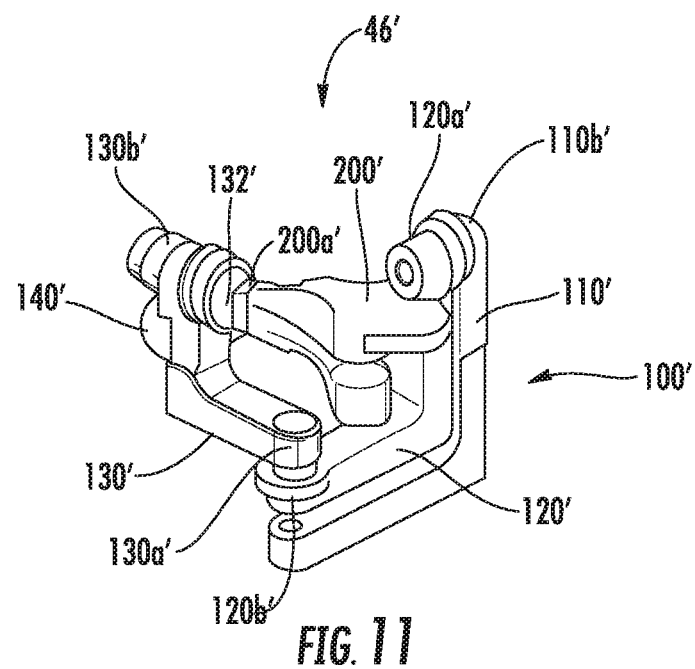
FIG. 11 is a perspective view of a control arm assembly in accordance with another embodiment of the present disclosure.

Referring now to FIG. 11, another embodiment of a control arm assembly 46' is shown. While control arm assembly 46' is discussed singularly below, a person of ordinary skill in the art can readily appreciate that a user interface 40 of a robotic surgical system 1 (FIG. 1) may include a plurality of substantially identical control arm assemblies 46'. Control arm assembly 46' is substantially similar to control arm assembly 46 and thus, is only described herein to the extent necessary to describe the differences in construction and operation thereof.

Control arm assembly 46' includes a gimbal 100' and a handle assembly 200' operably coupled to the gimbal 100'. The gimbal 100' includes an outer link 110', an intermediate link 120', and an inner link 130'. The outer link 110' includes a second end 110b' pivotably connected to a first end 120a' of the intermediate link 120', the intermediate link 120' includes a second end 120b' pivotably connected to a first end 130a' of the inner link 130', and the inner link 130' includes a second end 130b' having a connector 132' configured to releasably engage a distal end 200a' of the handle assembly 200' such that the handle assembly 200' is rotatable about "X," "Y," and "Z" axes as described above with regard to handle assembly 200 (FIGS. 1 and 2).

Figure 12:
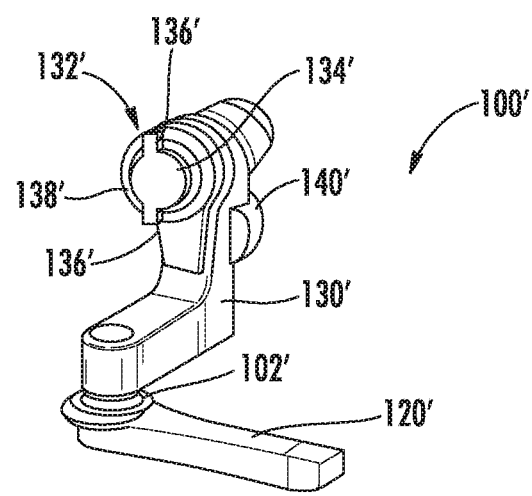
FIG. 12 is a perspective view, with parts removed, of a gimbal of the control arm assembly of FIG. 11.

Controllers (not shown) are disposed within each of the outer, intermediate, and inner links 110', 120', 130' to serialize encoder data to reduce wiring through the gimbal 100'. Secondary encoders, such as encoder 102' shown in FIG. 12, are disposed at the second ends 110b', 120b', 130b' of the outer, intermediate, and inner links 110', 120', 130' to sense the position of the outer, intermediate, and inner links 110', 120', 130'. The secondary encoders may be rotary encoders, such as magnetic, optical, or capacitive encoders, that convert rotational movement and/or angular position to a digital signal for processing by the processing unit 30 (FIG. 1). The secondary encoders can be potentiometers, hall sensors, optical sensors, or other suitable known sensors for measuring rotational movement and/or angular position.

A feedback assembly 140' may be mounted to the control arm 42 (FIG. 2), the outer, intermediate, or inner link 110', 120', 130' of the gimbal 100', and/or the handle assembly 200' to provide vibratory or haptic feedback to a clinician operating the handle assembly 200'. As shown, the feedback assembly 140' is a vibration voice coil assembly; however, the feedback assembly 140' can also be a piezoelectric vibration assembly, an off-balance motor feedback assembly, a wearable accessory worn by a clinician, or other suitable known vibration assembly. For a detailed discussion of the construction and operation of an exemplary vibration voice coil assembly, reference may be made to commonly owned U.S. Provisional Patent Application Ser. No. 62/248,516, filed Nov. 13, 2015, now International Application Serial No. PCT/US16/58970, filed Oct. 27, 2016, the entire content of each of which is incorporated herein by reference.

As shown in FIG. 12, in conjunction with FIG. 11, the connector 132' of the gimbal 100' includes a flanged outer edge 134' that is substantially semi-circular in shape, and opposed detents 136' defined at terminal ends of the flanged outer edge 134' that form a quick connect/disconnect interface, such as a tongue and groove connector or a bayonet coupling, with the distal end 200a' of the handle assembly 200' to releasably engage the handle assembly 200' to the gimbal 100'. A guide post 138' extends distally from the connector 132' and may be keyed to a through hole (not shown) defined in the distal end 200a' of the handle assembly 200'.

The connector 132' of the gimbal 100' allows a clinician to change the handle assembly 200' of the control arm assembly 46', such as with handle assembly 200 of FIG. 3, depending upon, for example, the desired size of a handle for ergonomic fit with the hand of the clinician and/or the type of handle desired for use to control a tool 20 of the robot system 10 (FIG. 1). The removability of the handle assembly 200' from the control arm assembly 46' allows a clinician to use a custom made handle assembly and/or different kinds of handle assemblies for different surgical applications. For example, a pistol grip style handle assembly (see e.g., FIG. 2) may be used for general surgery, while a smaller, pincher style handle assembly may be preferred for other surgical procedures, such as cardiac procedures, while yet other different style handle assemblies may be preferred or required from other surgical procedures, such as neurosurgery, microsurgery, or orthopedic surgery, for example.

As detailed above and shown in FIG. 1, the user interface 40 is in operable communication with the robot system 10 to perform a surgical procedure on a patient "P"; however, it is envisioned that the user interface 40 may be in operable communication with a surgical simulator (not shown) to virtually actuate a robot system and/or tool in a simulated environment. For example, the surgical robot system 1 may have a first mode where the user interface 40 is coupled to actuate the robot system 10 and a second mode where the user interface 40 is coupled to the surgical simulator to virtually actuate a robot system. The surgical simulator may be a standalone unit or be integrated into the processing unit 30. The surgical simulator virtually responds to a clinician interfacing with the user interface 40 by providing visual, audible, force, and/or haptic feedback to a clinician through the user interface 40. For example, as a clinician interfaces with the handle assemblies 200, the surgical simulator moves representative tools that are virtually acting on tissue at a simulated surgical site.

In embodiments in which the user interface includes removable handle assemblies, such as the handle assembly 200' shown in FIG. 11, the handle assemblies may be used in a standalone mode for surgical simulation by removing them from the user interface and electrically coupling the handle assemblies to a surgical simulator (not shown). The handle assemblies may be operably connected to the surgical simulator via a thin, flexible wire for motor power and sending and receiving of control signals between the handle assemblies and the surgical simulator. The position of the handle assemblies are tracked in 3D space (XYZ, and roll, pitch, and yaw) using a 3D tracking system, such as a magnetic or optical 3D tracking system, to measure the position of the handle assemblies. Such a configuration provides a clinician with a portable surgical simulator for use in any location, such as their home or office. It is envisioned that the surgical simulator may allow a clinician to practice a surgical procedure before performing the surgical procedure on a patient. In addition, the surgical simulator may be used to train a clinician on a surgical procedure. Further, the surgical simulator may simulate "complications" during a proposed surgical procedure to permit a clinician to plan a surgical procedure.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A control arm assembly for controlling a robot system, comprising:
   a gimbal moveable and rotatable about three axes; and
   a handle assembly coupled to the gimbal, the handle assembly including a body portion having a controller disposed therein and a first actuator disposed thereon, the first actuator including a proximal portion and a distal portion, the first actuator having a biased position in which the distal portion extends laterally away from the body portion and wherein application of a force on the distal portion in a direction towards the body portion moves the first actuator to an actuated position in which the proximal portion is moved laterally away from the body portion, the first actuator mechanically coupled to the controller via a four-bar linkage such that actuation of the first actuator causes mechanical movement of a component of the controller which is converted by the controller into an electrical signal.

2. The control arm assembly of claim 1, wherein a first link of the four-bar linkage is secured to the proximal portion of the first actuator.

3. The control arm assembly of claim 2, wherein the four-bar linkage further includes a second link fixedly disposed within the body portion of the handle assembly and operably connected to the controller, and third and fourth links pivotably coupled to the first and second links.

4. The control arm assembly of claim 3, wherein the component of the controller is a first gear, the second link of the four-bar linkage includes a second gear attached to a shaft rotatably disposed within the second link, the second gear of the second link meshingly engaged with the first gear of the controller, wherein movement of the fourth link causes rotational movement of the second gear of the second link which causes rotational movement of the first gear of the controller.

5. The control arm assembly of claim 4, wherein an end of the fourth link is non-rotatably coupled to the second gear of the second link.

6. The control arm assembly of claim 1, wherein the first actuator is disposed on an outer surface of the body portion of the handle assembly.

7. The control arm assembly of claim 6, wherein the handle assembly includes a strap extending over the distal portion of the first actuator.

8. The control arm assembly of claim 1, wherein the gimbal includes a connector releasably coupled to a distal end of the handle assembly.

9. The control arm assembly of claim 8, wherein the connector includes a flanged outer edge and opposed detents defined at terminal ends of the flanged outer edge for releasable engagement with the distal end of the handle assembly.

10. A handle assembly for controlling a robot system, comprising:
a body portion;
a controller disposed within the body portion;
a first actuator disposed on the body portion, the first actuator including a proximal portion and a distal portion, the first actuator having a biased position in which the distal portion extends laterally away from the body portion and wherein application of a force on the distal portion in a direction towards the body portion moves the first actuator to an actuated position in which the proximal portion is moved laterally away from the body portion; and
a four-bar linkage mechanically coupling the controller and the first actuator such that actuation of the first actuator causes mechanical movement of a component of the controller which is converted by the controller into an electrical signal.

11. The handle assembly of claim 10, wherein a first link of the four-bar linkage is secured to the proximal portion of the first actuator.

12. The handle assembly of claim 11, wherein the four-bar linkage further includes a second link fixedly disposed within the body portion and operably connected to the controller, and third and fourth links pivotably coupled to the first and second links.

13. The handle assembly of claim 12, wherein the component of the controller is a first gear, the second link of the four-bar linkage includes a second gear attached to a shaft rotatably disposed within the second link, the second gear of the second link meshingly engaged with the first gear of the controller, wherein movement of the fourth link causes rotational movement of the second gear of the second link which causes rotational movement of the first gear of the controller.

14. The handle assembly of claim 13, wherein an end of the fourth link is non-rotatably coupled to the second gear of the second link.

15. The handle assembly of claim 10, wherein the first actuator is disposed on an outer surface of the body portion.

16. The handle assembly of claim 15, further comprising a strap extending over the distal portion of the first actuator.

* * * * *